United States Patent
Lieberman (10) Patent No.: US 10,957,426 B1
(45) Date of Patent: Mar. 23, 2021

(54) COMPUTER-EXECUTABLE APPLICATION THAT FACILITATES MULTI-FACTOR AUTHENTICATION

(71) Applicant: Allscripts Software, LLC, Raleigh, NC (US)

(72) Inventor: Yuval Lieberman, Nevatim (IL)

(73) Assignee: ALLSCRIPTS SOFTWARE, LLC, Raleigh, NC (US)

(*) Notice: Subject to any disclaimer, the term of this patent is extended or adjusted under 35 U.S.C. 154(b) by 337 days.

(21) Appl. No.: 15/895,571

(22) Filed: Feb. 13, 2018

(51) Int. Cl.
*G16H 10/60* (2018.01)
*H04W 12/06* (2021.01)

(52) U.S. Cl.
CPC ............ *G16H 10/60* (2018.01); *H04W 12/06* (2013.01)

(58) Field of Classification Search
CPC ............................... G16H 10/60; H04W 12/06
See application file for complete search history.

(56) References Cited

U.S. PATENT DOCUMENTS

| | | | |
|---|---|---|---|
| 8,909,660 | B2 | 12/2014 | Campbell et al. |
| 8,935,769 | B2* | 1/2015 | Hessler .............. H04L 63/0869 726/7 |
| 8,973,091 | B2* | 3/2015 | Ting ....................... H04L 63/08 726/1 |
| 9,390,228 | B2 | 7/2016 | Reid |
| 9,805,213 | B1 | 10/2017 | Kragh |
| 2010/0324936 | A1 | 12/2010 | Vishnubhatla et al. |
| 2012/0089518 | A1 | 4/2012 | Blonchek |
| 2013/0317848 | A1 | 11/2013 | Savin |
| 2016/0019354 | A1 | 1/2016 | Grant et al. |
| 2016/0110505 | A1 | 4/2016 | Symanski et al. |

(Continued)

OTHER PUBLICATIONS

Contextual could overtake two-factor authentication, Enterprise Management 360 (Dec. 22, 2016) (Year: 2016).*

(Continued)

*Primary Examiner* — Jonathan Ng
*Assistant Examiner* — Jordan L Jackson
(74) *Attorney, Agent, or Firm* — Medley, Behrens & Lewis, LLC (57) ABSTRACT

Described herein are various technologies pertaining to authenticating, via a two-factor authentication method, the identity of a user requesting access to a medical application such as an electronic health record (EHR). The medical application, executing on a server computing device, authenticates the user based upon log in credentials provided to a client computing device, and indicates to the client computing device that the user has been authenticated. The client computing device transmits a message to a helper application (executing on a second server computing device), where the message indicates that the user has logged into the medical application. The helper application can then request confirmation from the user (by transmitting a request to a mobile computing device of the user) that the user has logged into the medical application. In another example, the helper application can determine that the user has logged into the medical application based upon a comparison between geographic locations of the client computing device and the mobile computing device (without requiring explicit user feedback).

20 Claims, 7 Drawing Sheets

(56) References Cited

U.S. PATENT DOCUMENTS

2017/0161439 A1* 6/2017 Raduchel ............. G06Q 10/063
2017/0169168 A1   6/2017 Batchelor et al.

OTHER PUBLICATIONS

Admin Guide to Two-Factor Authentication, SalesForce (Oct. 12, 2016)(available at https://www.salesforce.com/content/dam/web/en_us/www/documents/white-papers/2fa-admin-rollout-guide.pdf) (Year: 2016).*
William Braithwaite, Why Two-Factor Authentication in Healthcare?, Anakam Inc. (Year: 2009).*
Jose Luis Fernandez-Aleman et al . . . Security and privacy in electronic health records: A systematic literature review, 46 J. of Biomedical Informatics 541-562 (Jan. 8, 2013) (Year: 2013).*
William Braithwaite, Why Two-Factor Authentication in Flealthcare?, Anakam Inc. (Year: 2009).*
Dasgupta et al., Adaptive Multifactor Authentication (A-MFA) System, University of Memphis Center for Information Assurance (Nov. 21, 2016) (Year: 2016).*

* cited by examiner

COMPUTER-EXECUTABLE APPLICATION THAT FACILITATES MULTI-FACTOR AUTHENTICATION

BACKGROUND

The health care sector requires a healthcare provider to record, maintain, and synthesize large volumes of medical information unique to a given patient to provide the care necessary all while keeping the information safe and secure from unauthorized viewing, which can be cumbersome and inefficient. Healthcare workers at healthcare providers are frequently doctors, but may also be nurses, nurse's aides, dentists, dental assistants etc. As of Jan. 1, 2014, as part of the American Recovery and Reinvestment Act, healthcare providers were required to switch from paper record keeping to electronic record keeping, where computer-implemented electronic health record applications (EHRs) are configured to facilitate creation and maintenance of electronic health records (to comply with the law).

EHRs are utilized in medical facilities across a variety of aspects of a medical practice. For example, and not by way of limitation, an EHR can include functionality related to a patient's medical history, diagnoses, medications, treatment plans, immunization dates, allergies, radiology images, and laboratory and test results. Conventional EHRs, however, are currently not well-suited for maintaining all pertinent information usable to treat a patient, and thus healthcare workers, when providing care to a patient, may navigate through multiple software applications to acquire such information. For example, a first EHR may be used to maintain lab and test results, while a second EHR may be used to maintain radiology images, and a third EHR may be used to maintain general health information, such as medical history. In another example, a healthcare worker may simultaneously work for several healthcare providers, or may be a contactor who is contracted with several different healthcare providers, and thus the healthcare worker must employ multiple EHRs. This creates efficiency problems, as the healthcare worker must adeptly navigate through multiple software platforms quickly to provide care, which increases the risk of missing pertinent information that could alter the treatment of a patient. In addition, conventional EHRs do not allow for integration of reminders or notifications generated by other EHRs (as each EHR has its own logic).

Still further, conventional EHRs are ill-equipped to facilitate secure communication between different healthcare workers who are not employed by the same healthcare provider. For instance, an EHR of one healthcare provider may include data compiled by a clinical psychologist, wherein such data may be usable by a primary care physician to treat a patient (where the primary care physician uses a second EHR). Health Information Exchanges (HIEs) are conventionally used for exchange of data, but can be burdensome to EHR users.

Moreover, some conventional EHRs are not well-equipped to identify when user credentials are breached. For instance, a malicious entity may acquire authentication data of a healthcare provider—some EHRs are not well-equipped to detect such a security breach, particularly when the malicious entity is not physically present at a healthcare site.

SUMMARY

The following is a brief summary of subject matter that is described in greater detail herein. This summary is not intended to be limiting as to the scope of the claims.

Described herein are various technologies that are well-suited for use in a healthcare environment. More specifically, described herein are various technologies pertaining to a computer-executable helper application that can be executed simultaneously with an EHR, where the helper application is configured to present relevant information about a patient to a healthcare worker, and further where the helper application provides two-factor authentication to ensure that a malicious entity has not used user credentials of the healthcare worker to access the EHR.

In an exemplary embodiment, a client computing device executes a client EHR (which may be a standalone application or execute in a web browser), and a user of the client computing device (a healthcare worker) provides user credentials (e.g., username and password) to the client EHR. The client computing device, responsive to the client EHR receiving the user credentials, transmits the user credentials to a server computing device executing a server EHR (where, collectively, client EHRs and the server EHR may be referred to as an EHR). The server EHR authenticates the healthcare worker based upon the user credentials, whereupon the healthcare worker can interact with the client EHR to retrieve electronic data about a patient and generate electronic data about the patient.

The client computing device further executes a context identifier application, which receives data about context changes (e.g., where a context change occurs each time that the client EHR has retrieved data about a different patient). For example, when the client EHR retrieves data about a patient, the client EHR can output a context change message that comprises a unique identifier for the patient and a unique identifier for the healthcare worker, and the context identifier application can receive such context change message. The context identifier application, responsive to receiving the context change message, causes the client computing device to transmit the unique identifiers to a second server computing device that executes a server helper application. The server helper application, responsive to receiving the unique identifiers, identifies a registered user of the server helper application who is mapped to the unique identifier for the healthcare worker, and ascertains an identifier (e.g., telephone number or client helper application identifier) of a mobile computing device (e.g., mobile telephone) that is assigned to the healthcare worker.

The server helper application then causes the second server computing device to transmit a notification to the mobile computing device assigned to the healthcare worker, wherein the notification includes a request for the geographic location of the mobile computing device. The mobile computing device executes a client helper application, which receives the notification and causes the mobile computing device to transmit its geographic location (e.g., geographic coordinates output by a global positioning system (GPS) sensor) to the second server computing device. When the geographic location of the mobile computing device is different from an expected geographic location of the mobile computing device (e.g., where the mobile computing device is over a threshold distance from the client computing device that received the user credentials), the server helper application causes the client helper application to issue an alert to the mobile computing device, wherein the healthcare worker who is using the mobile computing device can provide input to the mobile computing device, thereby responding to the alert. For example, the mobile computing device may receive confirmation from the healthcare worker that the healthcare worker has set forth the user credentials and logged into the EHR, and the client helper application can cause the mobile computing device to transmit the confirmation to the server helper application. In another example, the mobile computing device can receive an indication from the healthcare worker that the healthcare worker has not attempted to log into the EHR, and the client helper application can transmit an indication to the server helper application that a security breach has occurred. The server application, in response to receipt of this indication (or when no confirmation is received in a threshold amount of time), can transmit a notification to an administrator of the EHR. Accordingly, the helper application (server and client helper application) provides security in addition to that natively provided by the EHR; moreover, the helper application provides this additional security regardless of the EHR being employed by the healthcare worker (e.g., the helper application is EHR agnostic).

The helper application is additionally configured to provide a unified graphical user interface by way of which information about patients of the healthcare worker can be shown, even in cases where the healthcare worker uses multiple EHRs. More specifically, as the server helper application receives data included in each context change message, the server helper application can maintain a list of patients who have had an encounter with the healthcare worker. The server helper application can cause the second server computing device to transmit this list to one or more mobile computing devices that execute the client helper application. Therefore, even if the healthcare worker interacted with three different patients by way of three different EHRs, the client helper application can present a list that includes each of the three patients.

Still further, the graphical user interface (GUI) of the client helper application can include a header field, wherein information about a patient and/or healthcare worker is displayed in the header field. For instance, the header field can display a list of patients with whom the healthcare worker has had an encounter, wherein each patient in the list can have corresponding thereto an indication of when the patient was seen, demographic information about the patient, whether the patient is marked for reminders, and so forth. The GUI of the helper application can include buttons or other graphical indicia such that, when a button (for example) is selected, the client helper application initiates a supplemental action.

Exemplary supplemental actions include transmission of referral data to another care provider (e.g., who works for a healthcare enterprise different from the healthcare enterprise that employs the healthcare worker) for consultation. Selecting this action causes a secure session to be instantiated between the server helper application and a computer-executable application employed by a healthcare worker to whom the patient is being referred. In another example, selecting such action causes a secure session to be instantiated between the server EHR and a computer-executable application employed by the healthcare worker to whom the patient is being referred. Responsive to the secure session being instantiated, pertinent patient information is (securely) transmitted to the computer-executable application employed by the healthcare worker to whom the patient is being referred. Another exemplary supplemental action is setting calendar reminders for patients, where text can be entered as well as a date and time to remind the health care worker and the patient in question of a follow-up. Yet another exemplary supplemental action is initiating a communication with a selected patient, such as sending the patient a message (e.g., email, SMS message, etc.) and/or initiating a telephone call, depending on a preference of the patient.

The above summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

DETAILED DESCRIPTION

Various technologies pertaining to a helper application that is configured to provide second-factor authentication for an EHR and are further configured to present contextually relevant data to a healthcare worker are now described with reference to the drawings, wherein like reference numerals are used to refer to like elements throughout. In the following description, for purposes of explanation, numerous specific details are set forth in order to provide a thorough understanding of one or more aspects. It may be evident, however, that such aspect(s) may be practiced without these specific details. In other instances, well-known structures and devices are shown in block diagram form in order to facilitate describing one or more aspects. Further, it is to be understood that functionality that is described as being carried out by certain system components may be performed by multiple components. Similarly, for instance, a component may be configured to perform functionality that is described as being carried out by multiple components.

Moreover, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form.

Further, as used herein, the terms "component" and "system" are intended to encompass computer-readable data storage that is configured with computer-executable instructions that cause certain functionality to be performed when executed by a processor. The computer-executable instructions may include a routine, a function, or the like. It is also to be understood that a component or system may be localized on a single device or distributed across several devices. Further, as used herein, the term "exemplary" is intended to mean serving as an illustration or example of something, and is not intended to indicate a preference.

The technologies described herein relate to a computer-executable application (referred to herein as a helper application) that executes in conjunction with an electronic health records application (EHR), wherein the helper application provides second factor authentication for a healthcare worker who is interfacing with the EHR, and additionally provides functionality that assists the healthcare worker with providing care to one or more patients of the healthcare worker. As will be described in greater detail below, the helper application is a distributed application that includes client-side functionality and server-side functionality.

Pursuant to an example, a healthcare provider can employ an EHR, wherein the EHR is a distributed application that includes a client-side application (client EHR) executing on a client computing device and a server-side application (server EHR) executing on a server computing device, and further wherein the client EHR and the server EHR are in communication with one another. For instance, the client EHR can receive user credentials from a healthcare worker. The client EHR can transmit such data to the server EHR, which can authenticate the healthcare worker. The server EHR can transmit, to the client EHR, information to be presented to the healthcare worker, wherein the client EHR presents such information on a display of the client computing device. A mobile computing device (separate from the client computing device) can execute a client helper application, wherein the client helper application is in communication with a server helper application executing on a second server computing device. Responsive to the server EHR authenticating the healthcare worker based upon the user credentials, the helper application executing on the mobile computing device receives an indication that the EHR has authenticated the healthcare worker, and the client helper application can request confirmation from the healthcare worker that the healthcare worker has, in fact, set forth user credentials to the EHR.

The helper application is also configured to provide a graphical user interface (GUI), wherein the GUI of the helper application presents information that is relevant to the current context of the client EHR. Thus, in an example, the helper application can present data that is relevant to a patient whose record is being presented to the healthcare worker by way of the client EHR. The GUI of the helper application interface includes a ribbon, wherein the ribbon comprises a plurality of buttons, and further wherein each button corresponds to a respective supplemental action.

A supplemental action is configured to provide the healthcare worker with additional information about one or more patients and/or mechanisms to communicate with or about the one or more patients. For example, when the client EHR is presenting information about a patient to a healthcare worker (such as the patient's health record), an exemplary supplemental action enabled by the helper application can include a mechanism for calling a phone number of the patient, a mechanism for sending a text message to the patient, a mechanism for setting a reminder regarding the patient, and so forth. In another example, an exemplary supplemental action represented in the ribbon can include retrieval of population data that is relevant to the patient, wherein such data can be presented to the healthcare provider by way of the GUI of the helper application.

Figure 1:
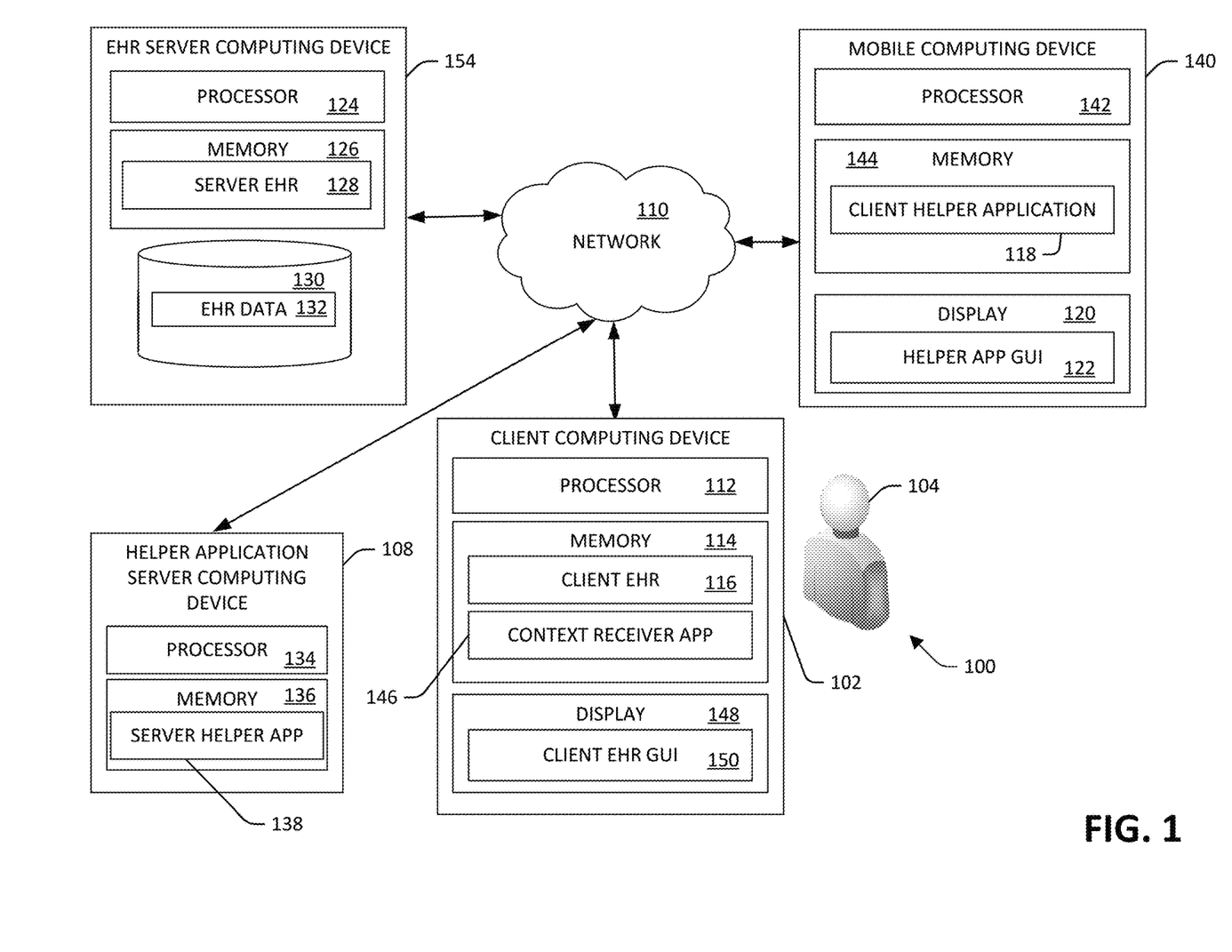
FIG. 1 is a functional block diagram of an exemplary system that facilitates second factor authentication and presentment of supplemental data to a user of an EHR.

Now referring to FIG. 1, an exemplary system 100 that facilitates providing second-factor authentication for an EHR when a healthcare worker sets forth user credentials to the EHR is illustrated. The system 100 includes a client computing device 102 that is operated by a healthcare worker 104 (e.g., a physician, a nurse, etc.). The client computing device 102 may be any suitable type of client computing device, including a desktop computing device, a laptop computing device, a tablet computing device, a mobile telephone, etc. The client computing device 102 is typically restricted to a healthcare environment (e.g., at a hospital or doctor's office), and is employed by the healthcare worker 104 when providing care to a patient.

The system 100 further includes an EHR server computing device 154 that is in communication with the client computing device 102 by way of a network 110, such as the Internet. The system 100 additionally comprises a mobile computing device 140, also operated by the healthcare provider 104. For example, the mobile computing device 140 may be a personal device of the healthcare worker 104, such as a mobile telephone of the healthcare worker 104. The system 100 also includes a helper application server computing device 108 that is in communication with the client computing device 102 and the mobile computing device 140 by way of the network 110. While FIG. 1 illustrates the client computing device 102 being in communication with the EHR server computing device 154 by way of the network 110, and also illustrates the client computing device 102 being in communication with the helper application server computing device 108 by way of the network 110, it is to be understood that the client computing device 102 can communicate with the EHR server computing device 154 and the helper application server computing device 108 over different networks.

The client computing device 102 includes a processor 112, a memory 114, and a display 148. The memory 114 stores instructions that are executed by the processor 112. More specifically, the memory 114 has loaded therein a client EHR 116 and a context receiver application 146, wherein the context receiver application 146 is configured to receive context change messages generated by the client EHR 116 (as described below). The client EHR 116, when executed by the processor 112, can cause a client EHR GUI 150 to be displayed on the display 148.

The mobile computing device 140 comprises a processor 142 and a memory 144. The memory 144 has loaded therein a client helper application 118. The mobile computing device 140 further comprises a display 120, wherein the client helper application 118 is configured to cause a helper application GUI 122 to be presented to the healthcare worker 104 on the display 120.

The EHR server computing device 154 comprises a processor 124 and memory 126, wherein the memory has a server EHR 128 loaded therein. The EHR server computing device 154 further includes a data store 130 that comprises EHR data 132, wherein the EHR data 132 comprises, for example, clinical data about numerous patients.

The helper application server computing device 108 comprises a processor 134 and memory 136, wherein the memory has a server helper application 138 loaded therein. As will be described in greater detail below, the server helper application 138 is configured to receive context change data from the context receiver application 146, and responsive to receiving such context change data, is further configured to direct a notification to the client helper application 118 executing on the mobile computing device 140, wherein the notification is based upon the context change data.

Exemplary operation of the system 100 is now set forth. The client EHR 116 executing on the client computing device 102 receives user credentials (e.g., username and password) from the healthcare worker 104, and causes the client computing device 102 to transmit the user credentials to the EHR server computing device 154. The server EHR 128 authenticates the healthcare worker 104 based upon the user credentials, and causes the server EHR computing device 154 to transmit data to the client EHR 116, wherein the data indicates that the healthcare worker 104 has been authenticated. The data received can include homepage data for the client EHR GUI 150, which can comprise a calendar for the healthcare worker 104, identities of patients that the healthcare worker is to see, etc. The client EHR 116, upon receipt of this data, updates the client EHR GUI 150 to include the homepage data.

The client EHR 116, based upon the data received from the server EHR 128, generates a context change message that indicates that a context of the client EHR 116 has changed (e.g., that the client EHR GUI 150 has been updated to display the homepage). Pursuant to an example, the context change message can conform to the Clinical Context Object Workgroup (CCOW) protocol, and can comprise an identifier for the healthcare worker 104. The context receiver application 146 receives the message generated by the client EHR 116 and causes the client computing device 102 to transmit data in the context change message to the helper application server computing device 108, whereupon the data in the context change message is received by the server helper application 138. In a non-limiting example, the context receiver application 146 can monitor a port on the client computing device 102 for CCOW messages, and can "intercept" the context change message when the context change message is received at the port. In another example, the context receiver application 146 can be registered with a CCOW context manager, and can receive the message from the CCOW context manager (subsequent to the CCOW context manager receiving the message from the client EHR 116).

The server helper application 138, based upon the identifier for the healthcare worker 104, retrieves data from a database (not shown) that identifies the mobile computing device (e.g., such as a telephone number, an identifier for the client helper application 118 installed on the mobile computing device 140, etc.). Responsive to retrieving such data from the database, the server helper application 138 causes the helper application server computing device 108 to transmit a notification to the mobile computing device 140, wherein the notification indicates that a person alleging to be the healthcare worker 104 has set forth the user credentials of the healthcare worker 104 to the server EHR 128. The client helper application 118 then causes a message to appear on the display 120, wherein the message indicates that a person alleging to be the healthcare worker 104 has set forth the user credentials of the healthcare worker 104 and has logged into the EHR. As the mobile computing device 140 can be the personal device of the healthcare worker 104, the healthcare worker 104 may typically carry the mobile computing device 140 and can provide input to the mobile computing device 140, where the input represents either confirmation that the healthcare worker 104 has logged into the EHR or a denial that the healthcare worker 104 has logged into the EHR.

The client helper application 118 subsequently causes the mobile computing device 140 to transmit a data packet to the server helper application 138, where the data packet is reflective of the input set forth by the healthcare worker 104 to the client helper application 118. When the data packet confirms that the healthcare worker 104 has logged into the EHR, then the server helper application 138 can record the time that the healthcare worker 104 logged into the EHR, but take no action that would result in restriction of use of the EHR by the healthcare worker 104. When, however, the data packet indicates that the healthcare worker 104 has not logged into the EHR (e.g., a person other than the healthcare worker 104 has set forth the user credentials of the healthcare worker 104 and logged into the EHR), then the server helper application server 138 can send a notification of security breach to an information technology (IT) department or other suitable contact, where such notification can be a text message, an instant message, an automated telephone call, or other suitable message.

In another embodiment, rather than immediately requesting input from the healthcare worker 104 when an indication is received that the server EHR 128 has received user credentials of the healthcare worker 104, the server helper application 138 can request a geographic location of the mobile computing device 140, and the mobile computing device 140 can respond with its geographic location (without requesting input from the healthcare worker 104). When the geographic location of the mobile computing device 140 corresponds to the geographic location of the client computing device 102 (e.g., which can indicate that the healthcare worker 104 is sitting at the client computing device 102), the server helper application 138 can authenticate that the healthcare worker 104 has provided his or her credentials to the server EHR 128. The geographic location of the client computing device 102 may be a predefined location (e.g., at a particular hospital). In another example, the geographic location of the client computing device 102 can be determined at runtime using any suitable technology (e.g., such as HTML5 geolocation technologies and/or WIN32 geolocation technologies).

Once the server EHR 128 has authenticated the healthcare worker 104 (and the client helper application 118 and server helper application 138 have acted in conjunction to provide second factor authentication for the EHR), the healthcare worker 104 can interact with the client EHR 116. For instance, the client EHR 116 can receive input from the healthcare worker 104 regarding to a specific patient (e.g., the healthcare worker 104 can set forth a query that identifies the patient). The client EHR 116 can then transmit the query to the EHR server computing device 154, whereupon the server EHR 128 executes the query over the EHR data 132 to generate search results (e.g., which can include electronic medical data for the patient). The server EHR 128 causes the EHR server computing device 154 to direct the search results to the client EHR 116. The electronic medical data for the patient can include data that identifies the patient, demographics about the patient, diagnoses, treatment plans, contact information for the patient, etc. The client EHR 116 updates the client EHR GUI 150 responsive to receiving the search results, such that at least a portion of the search results is presented in the client EHR GUI 150 on the display 148 of the client computing device 102.

This alteration to data displayed in the client EHR GUI 150 is a context change, and accordingly (as described above), the client EHR 116 generates a context change message (e.g., in accordance with the CCOW protocol). The context change message comprises the identifier for the healthcare worker 104, a unique identifier for the patient, and optionally other data about the patient, including patient demographics, contact information for the patient, etc. The context receiver application 146 receives the context change message and causes the client computing device 102 to transmit data in the context change message to the helper application server computing device 108, whereupon the server helper application 138 receives such data. The server helper application 138 can update a database (not shown) to indicate that the healthcare worker 104 has accessed data about the patient (and to further indicate a time when the healthcare worker has accessed the data about the patient), and therefore has provided care to such patient. Additionally, the server helper application 138 can cause the helper application server computing device 108 to transmit a message to the mobile computing device 140, wherein the message indicates that the healthcare worker 104 has accessed data about the patient from the server EHR 128. Further, optionally, the message can include a request for confirmation from the healthcare worker 104 that the healthcare worker 104 has accessed data about the patient from the server EHR 128 (thereby again providing second-factor authentication). Additionally or alternatively, the message can include a request for the geographic location of the mobile computing device 140, and when the geographic location of the mobile computing device 140 reported by the mobile computing device 140 to the server helper application 138 corresponds to the geographic location of the client computing device 102, the server helper application 138 can infer that the healthcare worker 104 has requested the data about the patient (using the client computing device) from the server EHR 128.

Still further, the message can include an identifier for the patient and contact information for the patient (e.g., a telephone number, email address, instant messaging alias, etc.). The client helper application 118 can cause such information to be presented in the helper application GUI 122, wherein the healthcare worker 104 can interact with the helper application GUI 122 to communicate with the patient, to ascertain when the healthcare worker 104 provided care to the patient, to set reminders about care for the patient, and so forth. More specifically, the client helper application 118 can support supplemental applications (not shown), where the supplemental applications can be launched by way of the client helper application 118. For instance, a supplemental application may be a telephone application on the mobile computing device 140, such that a telephone call to the patient can be initiated from the client helper application 118. In another example, a supplemental application may be a text messaging application on the mobile computing device 140, such that a text message to the patient can be initiated from the client helper application 118. In yet another example, the supplemental application may be a calendar application, such that a calendar entry can be generated by way of the client helper application 118.

The process described above can be repeated for each context change at the client EHR 116. Thus, each time that the healthcare worker 104 requests electronic data about a patient and the client EHR 116 generates a context change message, the context receiver application 146 receives the context change message and causes data in the context change message to be provided to the server helper application 138, which can in turn update the data in the database of the server helper application 138. Accordingly, the helper application GUI 122 can include a list of patients, where patients in the list can be ordered based upon times that the healthcare worker 104 retrieved electronic data about the patients from the server EHR 128. The healthcare worker 104 is then able to select a patient from the list, and can initiate a supplemental application with respect to the selected patient.

Figure 2:
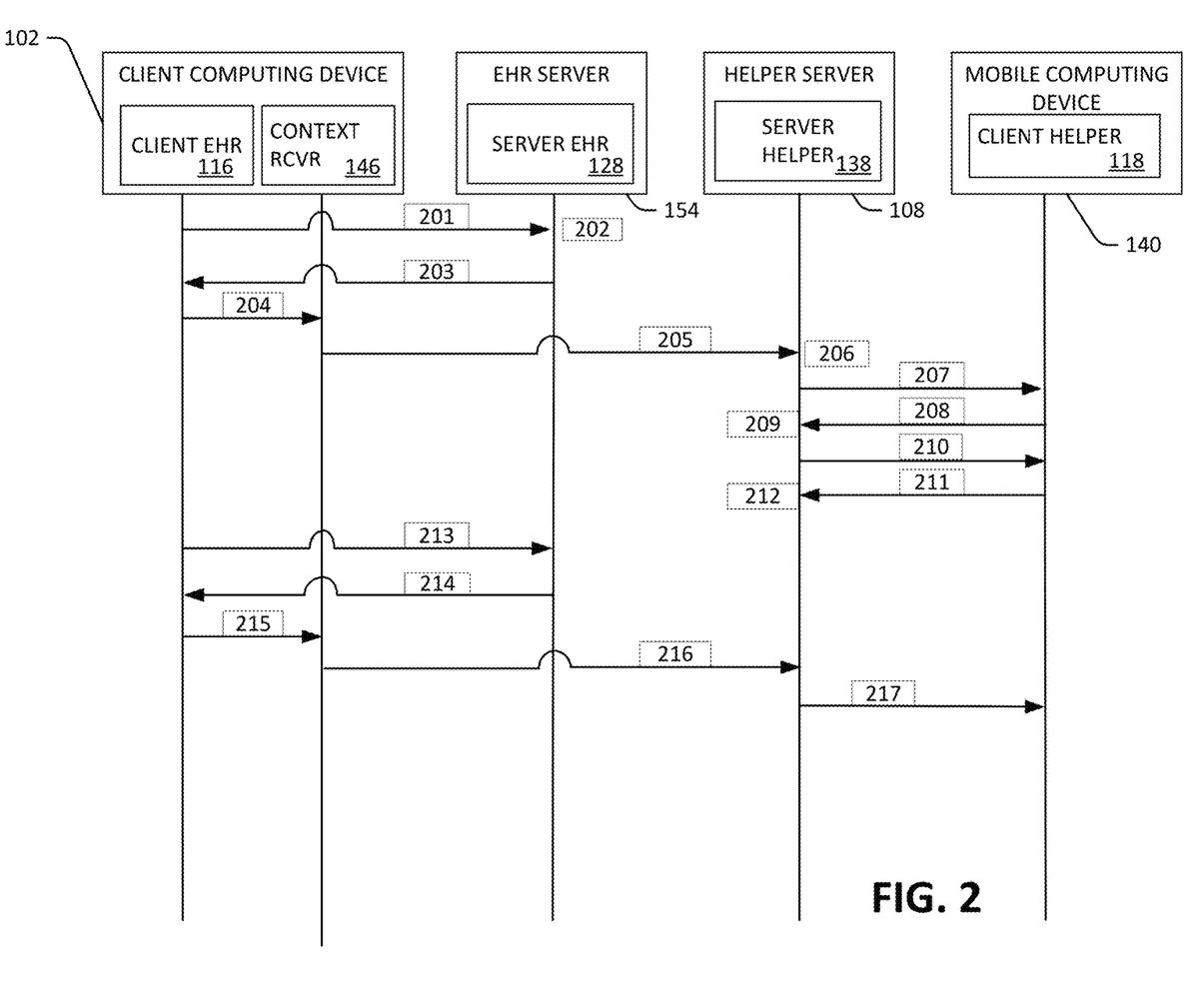
FIG. 2 depicts flow of information between computing devices of the exemplary system depicted in FIG. 1.

Referring now to FIG. 2, a flow diagram depicting flow of information within the exemplary system 100 is illustrated. The healthcare worker 104 inputs his or her user credentials into the client EHR 116 when prompted by a log-in screen of the client EHR 116. At 201, the client EHR 116 transmits a data packet comprising the user credentials to the server EHR 128. At 202, the server EHR 128 authenticates the healthcare provider 104 based upon the user credentials. At 203, the server EHR 128, responsive to authenticating the healthcare worker 104, transmits an update to the client EHR 116, wherein the update causes the client EHR 116 to make alterations as to what is shown in the client EHR GUI 150. At 204, the client EHR 116 outputs a context change message, which includes an identifier for the healthcare provider 104, indicating that a context change has occurred at the client EHR 116; as shown, the context receiver application 146 receives such context change message.

At 205, upon receipt of the context change message, the context receiver application 146 transmits data, including the identifier for the healthcare worker 104, to the server helper application 138, wherein the data indicates that the healthcare worker 104 has authenticated with the server EHR 128. At 206, the server helper application 138 uses the identifier for the healthcare worker 104 to retrieve an identifier for the client helper application 118 executing on the mobile computing device 140 of the healthcare worker 140, wherein the server helper application 138 retrieves such identifier from a database maintained by the server helper application 138. At 207, the server helper application 138 transmits a request for the geographic location to the mobile computing device 140 of the healthcare worker, wherein the request is directed to the mobile computing device 140 based upon the identifier for the client helper application 118. At 208, the client helper application 118 executing on the mobile computing device 140 responds to the request from the server helper application 138 with the location (e.g., GPS coordinates) of the mobile computing device 140. At 209, the server helper application 138 compares the reported location of the mobile computing device 140 with an expected location, such as the healthcare worker's 104 office, the hospital in which the healthcare provider 104 is employed, a known location of the client computing device 102, etc. As described above, the known location of the client computing device 102 may be predefined or can be determined through conventional geolocation technologies. When the reported location of the mobile computing device 140 does not match the expected location of the mobile computing device 140, at 210 the server helper application 138 transmits a message to the mobile computing device 140, wherein the message causes the client helper application 118 to solicit a response from the healthcare worker 104.

The client helper application 118 executing on the mobile computing device 140 requests the response from the healthcare worker 104 regarding whether the healthcare worker 104 attempted to authenticate to the server EHR 128 or whether there was a security breach and the healthcare provider's 104 credentials have been compromised. The healthcare worker 104 provides the response, and at 211 the client helper application 118 transmits the response to the server helper application 138. Based on the response, the server helper application 138 performs an appropriate action at 212. When the response indicates that there has been a security breach, the server helper application 138 transmits a message to a computing device of an administrator of the EHR, informing the administrator of the potential breach.

When the response indicates that the healthcare worker 104 (validly) authenticated with the server EHR 128, no further action is taken.

Subsequently, the healthcare worker 104 can interact with the client EHR 116. For example, at 213, responsive to the client EHR 116 receiving a request for electronic data about a patient, the client EHR 116 transmits a query for data about the patient to the server EHR 128. At 214, the server EHR 128 responds with the requested electronic data, resulting in another context change at the client EHR 116. At 215, the client EHR 116 generates a context change message, where the context change message comprises identifying information for the healthcare worker 104 and the patient for which electronic data was requested; the context receiver application 146 receives the context change message. At 216, the context receiver application 146 transmits a message to the server helper application 138, wherein the message includes the identifiers for the healthcare worker 104 and the patient for which the data was requested. The server helper application 138 can update its database, indicating that the healthcare worker 104 has provided care to the patient (and a time that such care was provided). At 217, the server helper application 138 can transmit data to the client helper application 118, wherein the client helper application 118, in response to receipt of such data, updates the helper application GUI 122 to indicate to the healthcare worker 104 that the healthcare worker 104 is providing care to the patient or has previously provided care to the patient.

As the healthcare worker 104 provides care to more patients, the client helper application 118 can present a list of patients in the helper application GUI 122; accordingly, the healthcare worker 104 can review the helper application GUI 122 to ascertain to whom the healthcare worker 104 has provided care over time. Moreover, as referenced above, the helper application GUI 122 can be configured to allow supplemental actions to be performed with respect to patients, such as setting reminders, making phone calls, sending text messages, and so forth. Still further, the helper application (server and client) are EHR agnostic; for example, the healthcare worker 104 may provide care in several different hospital units, each of which uses a different EHR. So long as the EHRs are able to generate context change messages, the server helper application 138 can track patients who have been cared for by the healthcare worker 104, even when the healthcare worker 104 provides care using several different EHRs. Finally, it is to be understood that the acts 213-217 can be repeated as the healthcare worker 104 continues to provide care for patients With reference now to FIG. 3, a functional block diagram of the client computing device 102 is illustrated. As indicated previously, the client EHR 116 is loaded in the memory 114 of the client computing device 102, and is executed by the processor 112. The client EHR 116 has a context manager 302, where the context manager 302 is configured to generate context change messages (e.g., in accordance with the CCOW protocol) when a context change occurs at the client EHR 116. In the example shown in FIG. 3, the context manager 302 generates a context change message 304, which can include an identity of the healthcare worker 104 who has authenticated with the server EHR 128 (by way of the client EHR 116) and, in some cases, an identifier for a patient.

Figure 3:
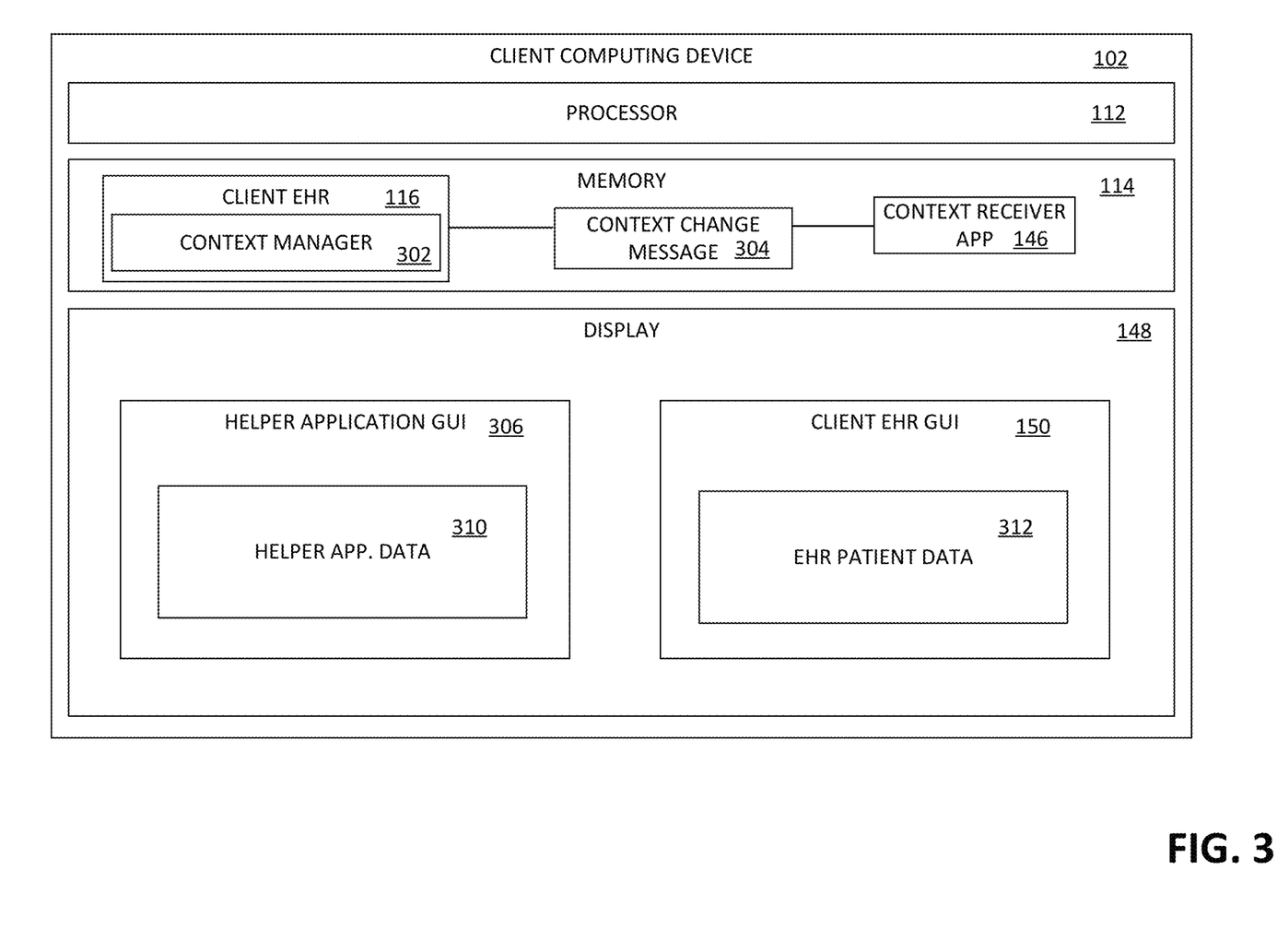
FIG. 3 depicts an exemplary client computing device.

In an exemplary embodiment, the context receiver application 146 can be included in a client helper application that is executed by the client computing device 102. Hence, the display 148 can include a helper application GUI 306, wherein the helper application GUI 306 presents information referenced above (e.g., identities of patients who have been previously provided care by the healthcare worker 104, mechanisms for communicating with those patients, and so forth). Thus, in an example, the helper application GUI 306 can present helper application data 310, which is relevant to EHR patient data 312 presented in the client EHR GUI 150. As will be described in greater detail below, the helper application GUI 306 can include several buttons, where the buttons are respectively representative of supplemental applications, such as sending electronic communications.

Figure 4:
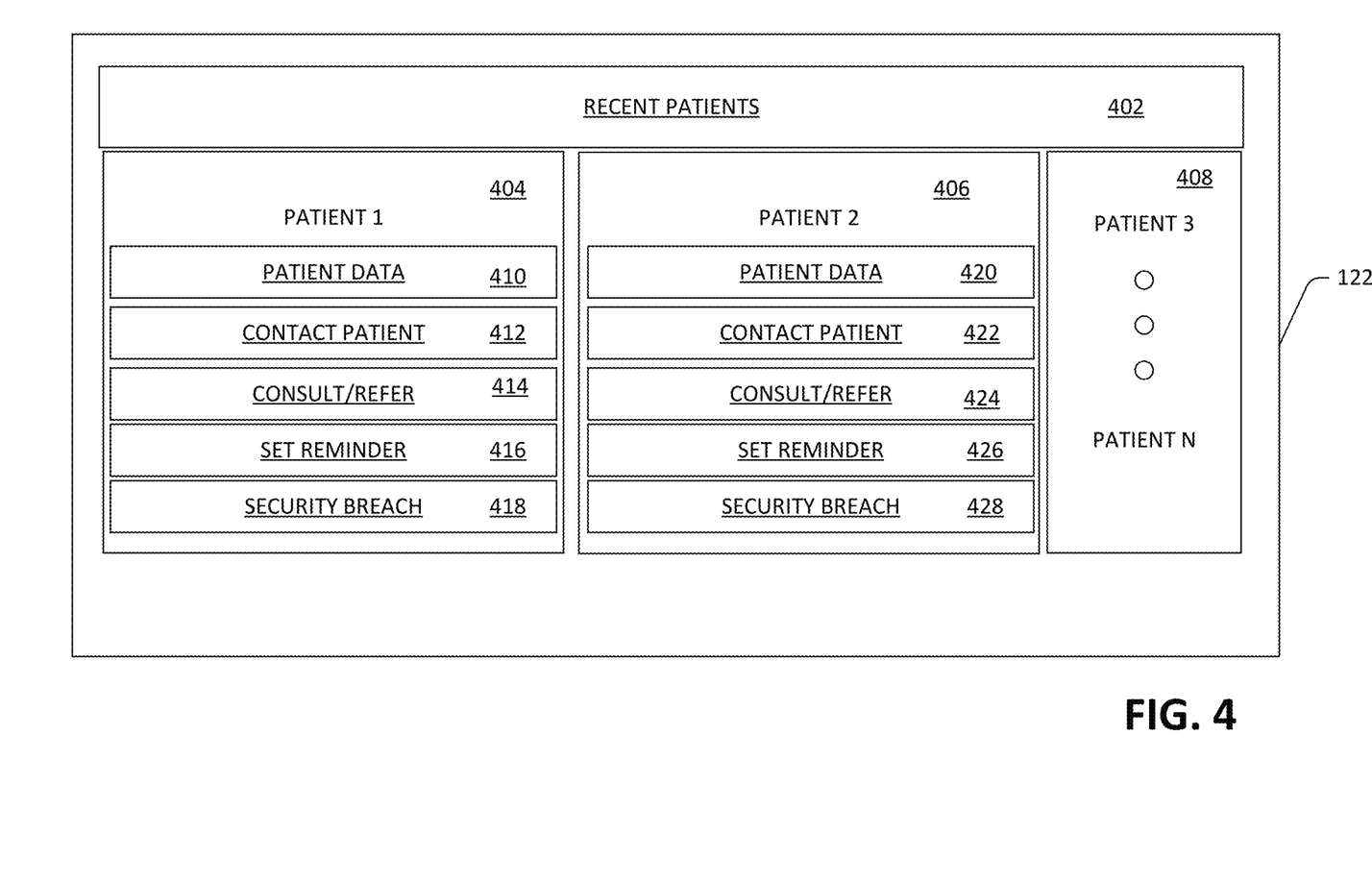
FIG. 4 depicts an exemplary helper application GUI.

With reference to FIG. 4, an exemplary illustration of the helper application GUI 122 as shown on the display 120 of the mobile computing device 140 is illustrated. In the example shown in FIG. 4, the helper application GUI 122 includes a ribbon 402. The ribbon 402 can indicate that the GUI 122 includes data about patients accessed on the client EHR 116 (and/or other EHRs) by the healthcare worker 104. In another example, the ribbon 402 can include a search field (not shown), wherein the healthcare worker 104 can set forth a query to the search field to search for patients. The GUI 122 can include graphical indicia 404 and 406 that respectively corresponds to a first patient and a second patient. Further, the GUI 122 can include a list of other patients 408, which includes patients previously interacted with by the healthcare worker 104 (e.g., the healthcare worker 104 has accessed data about the patients in the list 408 via one or more EHRs). By selecting a patient in the list 408, one of the graphical indicia 404 or 406 can be replaced with graphical indicia that corresponds to the selected patient.

The graphical indicia 404 and 406 each include selectable buttons. Specifically, the indicium 404 comprises buttons 410-418, while the indicium 406 comprises buttons 420-428. Responsive to selection of one of the buttons 410-418, for example by pressing the button with a finger or stylus, one of the plurality of supplemental applications that corresponds to the selected button can be launched, or the supplement application can be brought to the foreground. For example, the buttons 410-418 can include a patient data button 410, a contact patient button 412, a consult/refer button 414, a set a reminder button 416, and/or a security breach button 418. Similarly, the graphical indicium 406 can have selectable application buttons 420-428 which include: a patient data button 420, a contact patient button 422, a consult/refer button 424, a set a reminder button 426, and/or a security breach button 428. When the patient data button 410 or patient data button 420 is selected by the healthcare worker 104, additional information about the corresponding patient can be presented in the GUI 122, including demographic data, patient history, etc.

When the contact patient 412 button is selected by the healthcare worker 104, an electronic communications window can be presented in the GUI 122, wherein the healthcare worker 104 can set forth information in the communications window to transmit information to the first patient, such as patient data, appointment reminders, forms, etc. In another example, when the contact patient button 412 is selected, a communications application can be opened at the mobile computing device 140, wherein the communications application is provided with contact information for the first patient. When the consult/refer button 414 is selected, the client helper application 118 can cause an electronic communications window to be opened, wherein such window can be employed in connection with transmitting patient data to a different healthcare worker about the first patient (e.g., over a secure connection).

When the set reminder 416 button is selected, the client helper application 118 provides a mechanism that allows the healthcare worker 104 to set a reminder either for the healthcare worker 104 (e.g., for something such as to review lab results of the first patient, to check in with the first patient, etc.) or for the first patient (e.g., to remind the first patient regarding an upcoming appointment, prescription refill, etc.). When the security breach 418 button is selected by the healthcare worker 104, the client helper application 118 can initiate a communication to an administrator, as the healthcare worker 104 is asserting that the healthcare worker 104 never requested data about the first patient from an EHR. Such a circumstance would indicate someone has gained unauthorized access to the client EHR 116 using the healthcare provider's 104 credentials, which would constitute a security breach. The buttons 420-428 can be associated with similar functionality, except for the second patient rather than the first patient.

Figure 5:
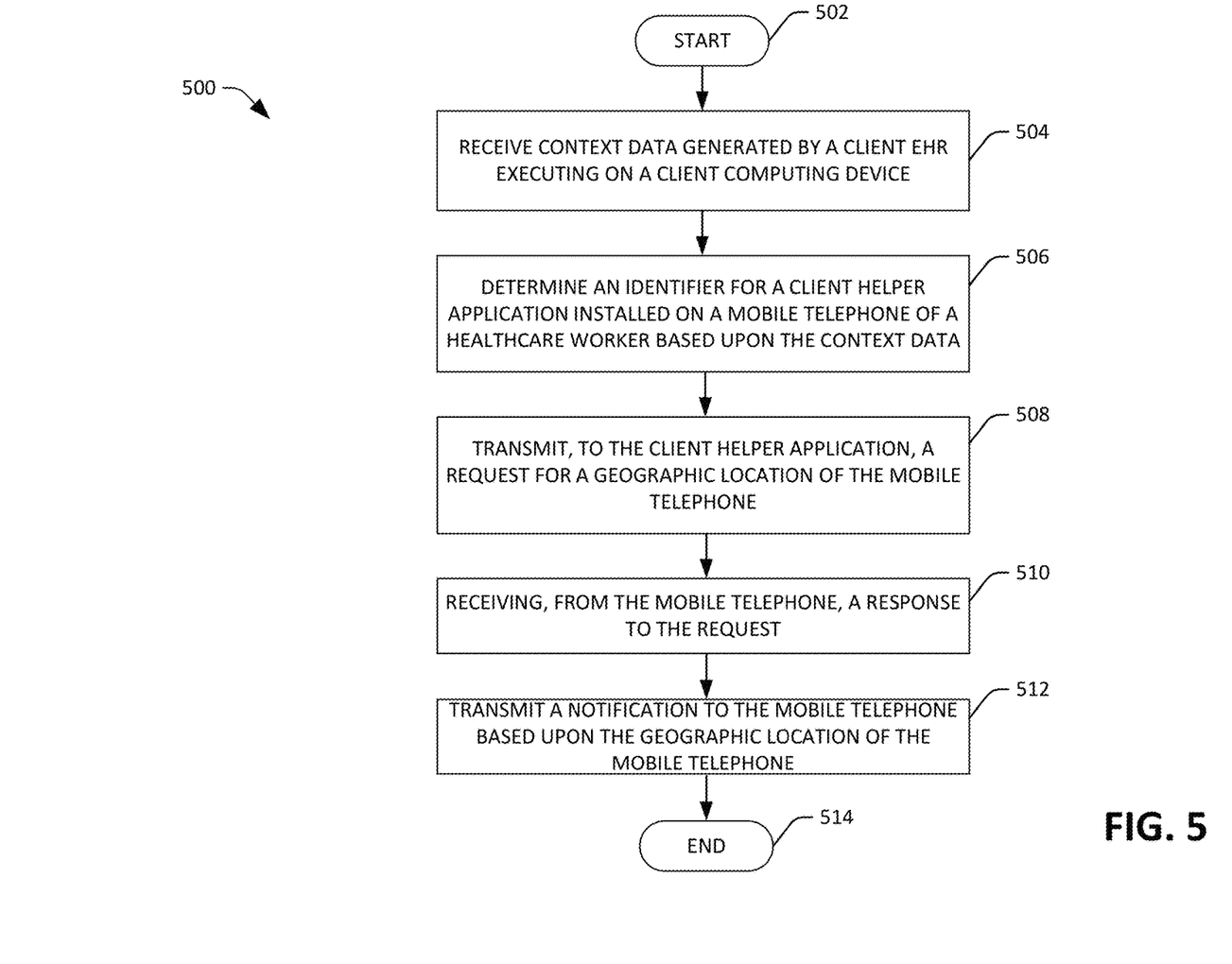
FIG. 5 is a flow diagram illustrating an exemplary methodology for performing second factor authentication for an EHR.
Figure 6:
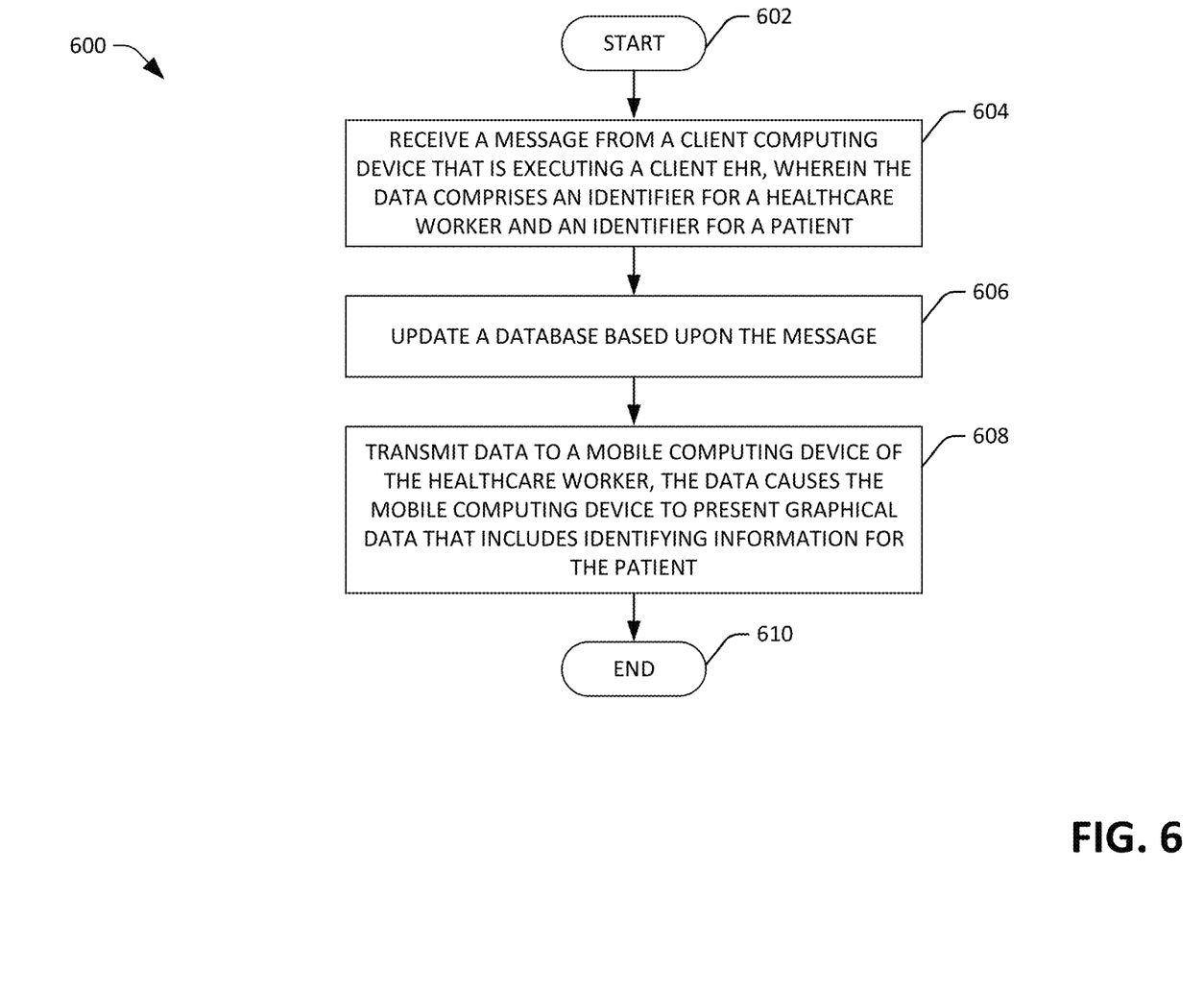
FIG. 6 is a flow diagram illustrating an exemplary methodology for updating a database of a helper application that executes simultaneously with an EHR.

FIG. 5 and FIG. 6 illustrate exemplary methodology relating to authenticating, via a second factor authentication method, the user of an EHR. While the methodology is shown and described as being a series of acts that are performed in a sequence, it is to be understood and appreciated that the methodology is not limited by the order of the sequence. For example, some acts can occur in a different order than what is described herein. In addition, an act can occur concurrently with another act. Further, in some instances, not all acts may be required to implement a methodology described herein.

Moreover, the acts described herein may be computer-executable instructions that can be implemented by one or more processors and/or stored on a computer-readable medium or media. The computer-executable instructions can include a routine, a sub-routine, programs, a thread of execution, and/or the like. Still further, results of acts of the methodologies can be stored in a computer-readable medium, displayed on a display device, and/or the like.

Now referring solely to FIG. 5, an exemplary methodology 500 that can be performed at the helper application server computing device 108 is illustrated. The methodology 500 begins at 502, and at 504 context data is received, wherein the context data is generated by a client EHR executing on a client computing device that has received user credentials from a healthcare worker who is operating the client computing device. For example, the client EHR can generate a context change message responsive to a context change occurring, and the context change message can include an identifier for the healthcare worker (and possibly an identifier for a patient). At 506, an identifier of a client helper application that is installed on a mobile telephone of the healthcare worker is determined based upon the identifier for the healthcare worker. Specifically, a database can be searched using the identifier for the healthcare worker, and the identifier of the client helper application can be retrieved. Using this identifier for the client helper application, at 508 a request is transmitted to the client helper application (and thus to the mobile telephone of the healthcare worker), where the request is for a geographic location of the mobile telephone.

At 510, a response to the request is received from the mobile telephone, wherein the response can include GPS coordinates. At 512, a notification is transmitted to the mobile telephone based upon the geographic location of the mobile telephone. For instance, when the geographic location of the mobile telephone is at an unexpected location (e.g., not proximate to the client computing device executing the client EHR), the notification can be a request for confirmation that the healthcare worker has logged into the EHR by way of the client computing device. In another example, when the geographic location of the mobile telephone is at an expected location, the notification can include information about a patient. The methodology 500 completes at 514. The methodology 500 completes at 512.

Now referring to FIG. 6, an exemplary methodology 600 that is executed at the helper application server computing device 108 is illustrated. The methodology 600 starts at 602, and at 604 a message is received from a client computing device that executes a client EHR, wherein the message comprises an identifier of a healthcare worker who is operating the client computing device, and further includes an identifier of a patient whose electronic medical data is displayed on a GUI of the client EHR. At 606, a database is updated to indicate that the healthcare worker has provided care for the patient, and to further indicate a time when the electronic medical data was displayed on the GUI of the client EHR. At 608, data is transmitted to a mobile computing device of the healthcare worker, wherein the data, when received by the mobile computing device, causes the mobile computing device to present graphical data, the graphical data includes identifying information for the patient. The methodology 600 completes at 610.

Figure 7:
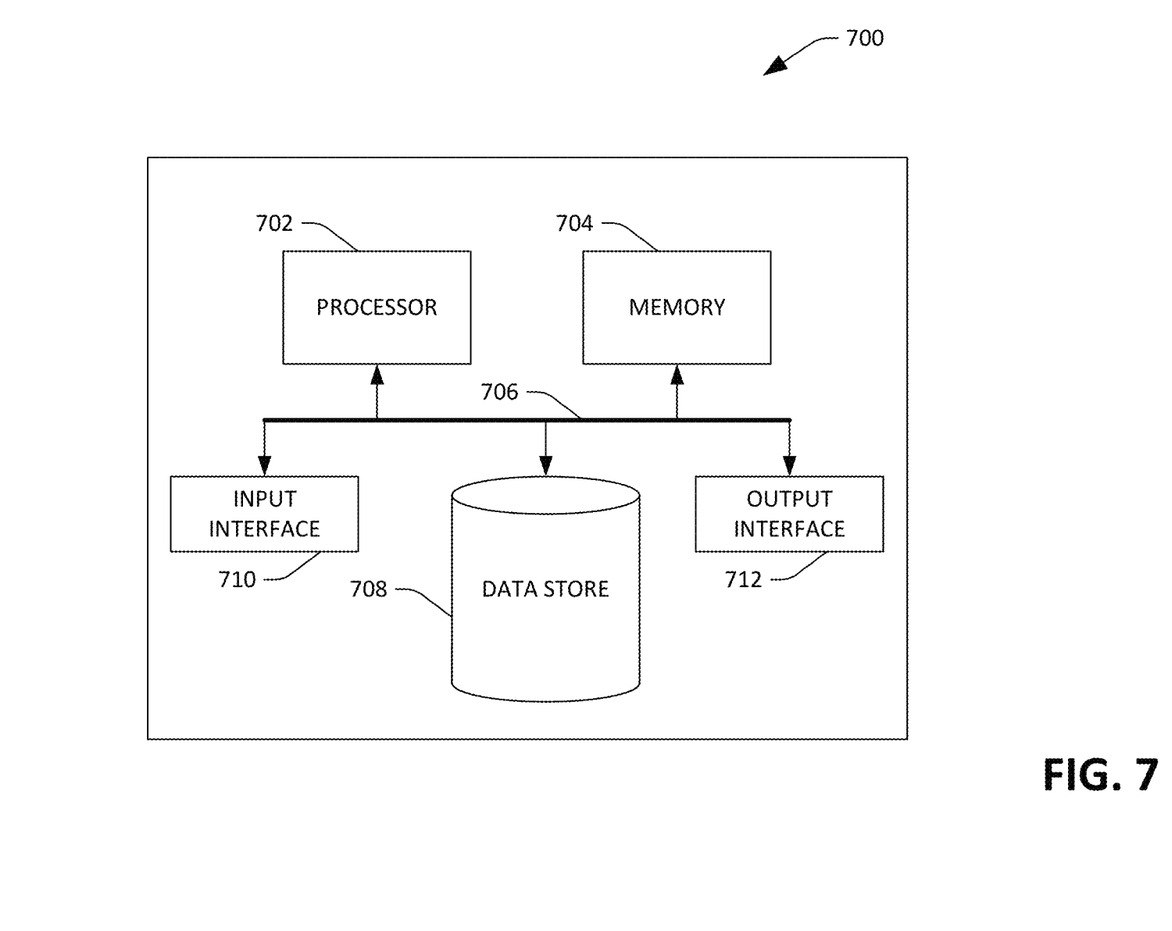
FIG. 7 is an exemplary computing system.

Referring now to FIG. 7, a high-level illustration of an exemplary computing device 700 that can be used in accordance with the systems and methodologies disclosed herein is illustrated. For instance, the computing device 700 may be used in a system that executes an EHR. By way of another example, the computing device 700 can be used in a system that executes a helper application and/or supplemental application. The computing device 700 includes at least one processor 702 that executes instructions that are stored in a memory 704. The instructions may be, for instance, instructions for implementing functionality described as being carried out by one or more components discussed above or instructions for implementing one or more of the methods described above. The processor 702 may access the memory 704 by way of a system bus 706. In addition to storing executable instructions, the memory 704 may also store patient-centric data, aggregated patient data, claim conditions, etc.

The computing device 700 additionally includes a data store 708 that is accessible by the processor 702 by way of the system bus 706. The data store 708 may include executable instructions, patient data, reminders, electronic messages, etc. The computing device 700 also includes an input interface 710 that allows external devices to communicate with the computing device 700. For instance, the input interface 710 may be used to receive instructions from an external computer device, from a user, etc. The computing device 700 also includes an output interface 712 that interfaces the computing device 700 with one or more external devices. For example, the computing device 700 may display text, images, etc. by way of the output interface 712.

It is contemplated that the external devices that communicate with the computing device 700 via the input interface 710 and the output interface 712 can be included in an environment that provides substantially any type of user interface with which a user can interact. Examples of user interface types include graphical user interfaces, natural user interfaces, and so forth. For instance, a graphical user interface may accept input from a user employing input device(s) such as a keyboard, mouse, remote control, or the like and provide output on an output device such as a display. Further, a natural user interface may enable a user to interact with the computing device 700 in a manner free from constraints imposed by input device such as keyboards, mice, remote controls, and the like. Rather, a natural user interface can rely on speech recognition, touch and stylus recognition, gesture recognition both on screen and adjacent to the screen, air gestures, head and eye tracking, voice and speech, vision, touch, gestures, machine intelligence, and so forth.

Additionally, while illustrated as a single system, it is to be understood that the computing device 700 may be a distributed system. Thus, for instance, several devices may be in communication by way of a network connection and may collectively perform tasks described as being performed by the computing device 700.

Various functions described herein can be implemented in hardware, software, or any combination thereof. If implemented in software, the functions can be stored on or transmitted over as one or more instructions or code on a computer-readable medium. Computer-readable media includes computer-readable storage media. A computer-readable storage media can be any available storage media that can be accessed by a computer. By way of example, and not limitation, such computer-readable storage media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, include compact disc (CD), laser disc, optical disc, digital versatile disc (DVD), floppy disk, and Blu-ray disc (BD), where disks usually reproduce data magnetically and discs usually reproduce data optically with lasers. Further, a propagated signal is not included within the scope of computer-readable storage media. Computer-readable media also includes communication media including any medium that facilitates transfer of a computer program from one place to another. A connection, for instance, can be a communication medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio and microwave are included in the definition of communication medium. Combinations of the above should also be included within the scope of computer-readable media.

Alternatively, or in addition, the functionally described herein can be performed, at least in part, by one or more hardware logic components. For example, and without limitation, illustrative types of hardware logic components that can be used include Field-programmable Gate Arrays (FPGAs), Program-specific Integrated Circuits (ASICs), Program-specific Standard Products (ASSPs), System-on-a-chip systems (SOCs), Complex Programmable Logic Devices (CPLDs), etc.

What has been described above includes examples of one or more embodiments. It is, of course, not possible to describe every conceivable modification and alteration of the above devices or methodologies for purposes of describing the aforementioned aspects, but one of ordinary skill in the art can recognize that many further modifications and permutations of various aspects are possible. Accordingly, the described aspects are intended to embrace all such alterations, modifications, and variations that fall within the spirit and scope of the appended claims. Furthermore, to the extent that the term "includes" is used in either the detailed.

What is claimed is:

1. A server computing device, comprising:
   a processor; and
   memory that stores a server helper application that, when executed by the processor, causes the processor to perform acts comprising:
   receiving a context change notification generated by a client electronic health record application (client EHR) executing on a client computing device, the context change notification indicating that the client EHR has received input indicating that a graphical user interface (GUI) of the client EHR is to be updated to display patient data for a patient that is not currently displayed within the GUI, wherein a healthcare worker is currently logged into a server electronic health records application (server EHR) that is in communication with the client EHR;
   responsive to receiving the context change notification, and based upon an identifier for the healthcare worker, determining an identifier for a client helper application that is registered with the server helper application as belonging to the healthcare worker, wherein the client helper application is installed on a mobile computing device of the healthcare worker;
   responsive to determining the identifier for the client helper application and based upon the identifier for the client helper application, transmitting a request for a geographic location of the mobile computing device to the client helper application installed on mobile computing device;
   subsequent to transmitting the request, receiving, from the mobile computing device, the geographic location of the mobile computing device;
   performing a comparison between the geographic location of the mobile computing device and an expected geographic location of the mobile computing device, wherein the comparison indicates that the mobile computing device is located over a threshold distance from the expected geographic location of the mobile computing device; and
   transmitting a notification to the mobile computing device, the notification requesting that the healthcare worker provide an indication as to whether the healthcare worker provided the input to the client EHR.

2. The server computing device of claim 1, wherein the context change notification comprises an identifier for the patient.

3. The server computing device of claim 1, wherein the mobile computing device is a mobile telephone carried by the healthcare worker.

4. The server computing device of claim 1, wherein the expected geographic location of the mobile computing device is a geographic location of the client computing device.

5. The server computing device of claim 1, wherein the expected geographic location of the mobile computing device is a predefined geographic location.

6. The server computing device of claim 1, the acts further comprising:
   subsequent to transmitting the notification to the mobile computing device, receiving a message from the mobile computing device that indicates that the healthcare worker did not provide the input to the client EHR; and
   responsive to receiving the message from the mobile computing device, transmitting a warning to a computing device operated by an administrator of a health enterprise that employs the healthcare worker.

7. A method performed by a processor of a server computing device that is executing a server helper application, the method comprising:
   receiving a context change notification generated by a client electronic health record application (client EHR) executing on a client computing device, the context change notification indicating that the client EHR has received input indicating that a graphical user interface (GUI) of the client EHR is to be updated to display patient data for a patient that is not currently displayed within the GUI, wherein a healthcare worker is currently logged into a server electronic health records application (server EHR) that is in communication with the client EHR;
   responsive to receiving the context change notification, and based upon an identifier for the healthcare worker, determining an identifier for a client helper application that is registered with the server helper application as belonging to the healthcare worker, wherein the client helper application is installed on a mobile computing device of the healthcare worker;
   responsive to determining the identifier for the client helper application and based upon the identifier for the client helper application, transmitting a request for a geographic location of the mobile computing device to the client helper application installed on mobile computing device;
   subsequent to transmitting the request, receiving, from the mobile computing device, the geographic location of the mobile computing device;
   performing a comparison between the geographic location of the mobile computing device and an expected geographic location of the mobile computing device, wherein the comparison indicates that the mobile computing device is located over a threshold distance from the expected geographic location of the mobile computing device; and
   transmitting a notification to the mobile computing device, the notification requesting that the healthcare worker provide an indication as to whether the healthcare worker provided the input to the client EHR.

8. The method of claim 7, wherein the context change notification comprises an identifier for the patient.

9. The method of claim 7, wherein the mobile computing device is a mobile telephone carried by the healthcare worker.

10. The method of claim 7, wherein the expected geographic location of the mobile computing device is a geographic location of the client computing device.

11. The method of claim 7, wherein the expected geographic location of the mobile computing device is a predefined geographic location.

12. The method of claim 7, further comprising:
   subsequent to transmitting the notification to the mobile computing device, receiving a message from the mobile computing device that indicates that the healthcare worker did not provide the input to the client EHR; and
   responsive to receiving the message from the mobile computing device, transmitting a warning to a computing device operated by an administrator of a health enterprise that employs the healthcare worker.

13. A computer-readable storage medium comprising a server helper application that, when executed by a processor, causes the processor to perform acts comprising:
   receiving a context change notification generated by a client electronic health record application (client EHR) executing on a client computing device, the context change notification indicating that the client EHR has received input indicating that a graphical user interface (GUI) of the client EHR is to be updated to display patient data for a patient that is not currently displayed within the GUI, wherein a healthcare worker is currently logged into a server electronic health records application (server EHR) that is in communication with the client EHR;
   responsive to receiving the context change notification, and based upon an identifier for the healthcare worker, determining an identifier for a client helper application that is registered with the server helper application as belonging to the healthcare worker, wherein the client helper application is installed on a mobile computing device of the healthcare worker;
   responsive to determining the identifier for the client helper application and based upon the identifier for the client helper application, transmitting a request for a geographic location of the mobile computing device to the client helper application installed on mobile computing device;
   subsequent to transmitting the request, receiving, from the mobile computing device, the geographic location of the mobile computing device;
   performing a comparison between the geographic location of the mobile computing device and an expected geographic location of the mobile computing device, wherein the comparison indicates that the mobile computing device is located over a threshold distance from the expected geographic location of the mobile computing device; and
   transmitting a notification to the mobile computing device, the notification requesting that the healthcare worker provide an indication as to whether the healthcare worker provided the input to the client EHR.

14. The computer-readable storage medium of claim 13, wherein the context change notification comprises an identifier for the patient.

15. The computer-readable storage medium of claim 13, wherein the client computing device is a second mobile computing device.

16. The computer-readable storage medium of claim 13, the acts further comprising:
   upon determining that the server helper application has not received the indication as to whether the healthcare worker provided the input to the client EHR within a threshold period of time, transmitting a warning to a computing device operated by an administrator of a health enterprise that employs the healthcare worker.

17. The computer-readable storage medium of claim 13, the acts further comprising:
   subsequent to transmitting the notification to the mobile computing device, receiving a message from the mobile computing device that indicates that the healthcare worker did not provide the input to the client EHR; and
   responsive to receiving the message from the mobile computing device, transmitting a warning to a computing device operated by an administrator of a health enterprise that employs the healthcare worker.

18. The computer-readable storage medium of claim 13, wherein the expected geographic location of the mobile computing device is a geographic location of the client computing device.

19. The computer-readable storage medium of claim 13, wherein the expected geographic location of the mobile computing device is a predefined geographic location.

20. The computer-readable storage medium of claim 13, wherein the mobile computing device is a mobile telephone carried by the healthcare worker.

* * * * *